United States Patent
DeBoef et al.

(10) Patent No.: US 11,045,561 B2
(45) Date of Patent: Jun. 29, 2021

(54) ROTAXANE-TYPE PROBE FOR MOLECULAR IMAGING

(71) Applicant: Rhode Island Council on Postsecondary Education, Warwick, RI (US)

(72) Inventors: Brenton DeBoef, Cumberland, RI (US); Ashvin Fernando, Kingston, RI (US)

(73) Assignee: University of Rhode Island Board of Trustees, Kingston, RI (US)

(*) Notice: Subject to any disclaimer, the term of this patent is extended or adjusted under 35 U.S.C. 154(b) by 78 days.

(21) Appl. No.: 15/939,261

(22) Filed: Mar. 28, 2018

(65) Prior Publication Data
US 2019/0101545 A1 Apr. 4, 2019

Related U.S. Application Data

(60) Provisional application No. 62/477,811, filed on Mar. 28, 2017.

(51) Int. Cl.
| | | |
|---|---|---|
| *A61K 49/18* | (2006.01) | |
| *C08L 5/16* | (2006.01) | |
| *C08G 83/00* | (2006.01) | |
| *G01N 33/68* | (2006.01) | |
| *C08B 37/16* | (2006.01) | |
| *A61K 49/10* | (2006.01) | |
| *C08L 101/00* | (2006.01) | |
| *G01N 33/58* | (2006.01) | |
| *G01N 33/00* | (2006.01) | |
| *G01R 33/28* | (2006.01) | |
| *G01R 33/56* | (2006.01) | |

(52) U.S. Cl.
CPC ............ *A61K 49/189* (2013.01); *A61K 49/10* (2013.01); *C08B 37/0015* (2013.01); *C08G 83/007* (2013.01); *C08L 5/16* (2013.01); *C08L 101/00* (2013.01); *G01N 33/6896* (2013.01); *C08L 2203/02* (2013.01); *G01N 33/0021* (2013.01); *G01N 33/582* (2013.01); *G01N 2800/2821* (2013.01); *G01R 33/282* (2013.01); *G01R 33/5601* (2013.01); *G01R 33/5605* (2013.01)

(58) Field of Classification Search
None
See application file for complete search history.

(56) References Cited

U.S. PATENT DOCUMENTS

| | | |
|---|---|---|
| 2005/0049383 A1 | 3/2005 | Takata et al. |
| 2006/0154254 A1 | 7/2006 | Kim et al. |
| 2010/0105099 A1* | 4/2010 | Dmochowski ... G01N 33/54373 435/29 |
| 2014/0350242 A1 | 11/2014 | Chiu et al. |
| 2015/0051393 A1 | 2/2015 | Chiu et al. |

OTHER PUBLICATIONS

Katz et al. Electromechanics of a redox-active rotaxane in a monolayer assembly on an electrode. 2004 J. Am. Chem. Soc. 126: 15520-15532. (Year: 2004).*

Adiri, T. et al. "Potential 129Xe-NMR biosensors based on secondary and tertiary complexes of a water-soluble pillar [5]arene derivative" Chem. Commun., 49, 7082-7084 (2013).

Hane, F. et al. "In vivo detection of cucurbit[6]uril, a hyperpolarized xenon contrast agent for a xenon magnetic resonance imaging biosensor" Sci. Rep. 7, 41027; doi: 10.1038/srep41027 (2017).

* cited by examiner

*Primary Examiner* — Jennifer Lamberski
(74) *Attorney, Agent, or Firm* — Milstein Zhang & Wu LLC; Duan Wu, Esq.

(57) ABSTRACT

The invention provides a novel method for synthesizing hyperpolarized xenon-129 (HP Xe) biosensors by using pseudo-rotaxane structures of gamma-cyclodextrin. These supramolecular complexes form novel ternary structures in the presence of HP Xe which can be detected via $^{129}$Xe MR spectroscopy and imaging techniques. The rotaxane-type complex can be tagged with an affinity label for detecting a target in a biological subject.

20 Claims, 11 Drawing Sheets
(10 of 11 Drawing Sheet(s) Filed in Color)

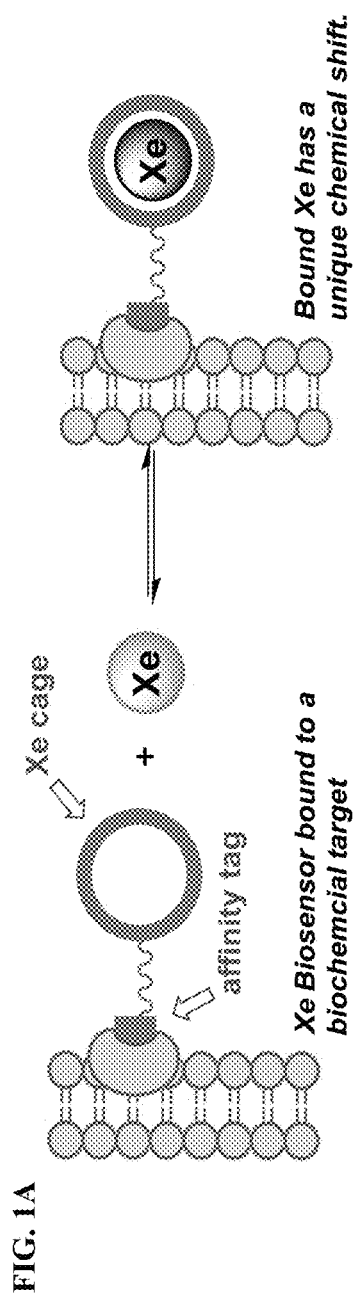
FIG. 1A
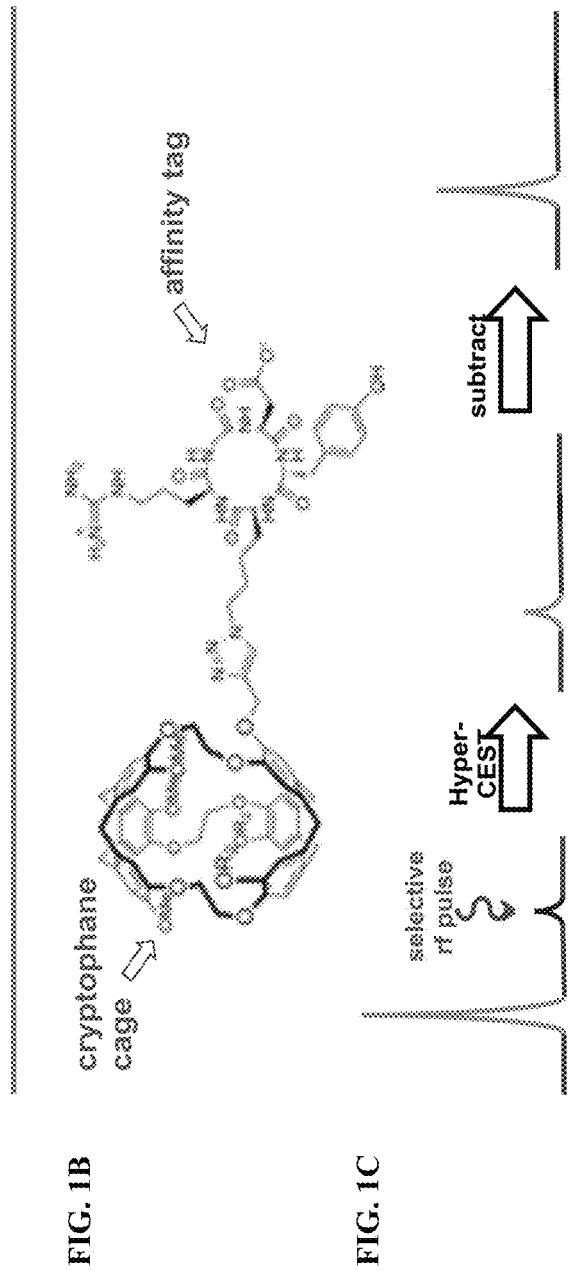
FIG. 1B
FIG. 1C
(Prior Art)

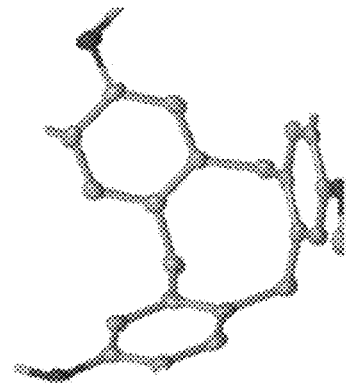
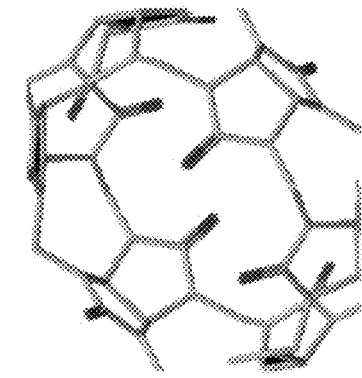
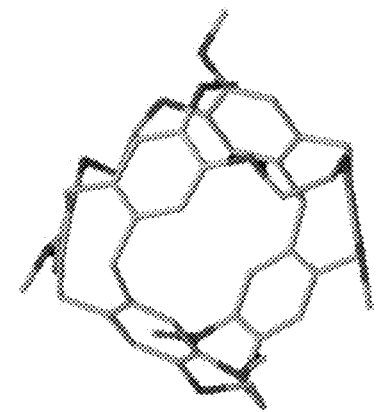
Ball - CrypA — Not water-soluble; Difficult to synthesize (<5% yield)
Tube – CB6 — Virtually impossible to functionalize; Captures Na⁺ ions
Bowl - CTV — Not water-soluble; Virtually impossible to functionalize
FIG. 3 (Prior Art)

| Pseudo-rotaxane (macrocycle + bar) | % Depletion[a] | δ (ppm)[a] |
|---|---|---|
| cucurbit[6]uril | | |
| + none | 67% | +128 |
| + C₆ diethylimidazolium bar (3) | 0% | - |
| + C₁₀ diethylimidazolium bar (1) | 0% | - |
| cucurbit[7]uril | | |
| + none | 0% | - |
| + C₅ diethylimidazolium bar (3) | 0% | - |
| cucurbit[8]uril | | |
| + none | 0% | - |
| + C₅ diethylimidazolium bar (3) | 0% | - |
| + C₁₀ diethylimidazolium bar (1) | 0% | - |
| decamethyl-pillar[5]arene | | |
| + none[c] | 0% | - |
| + C₅ diethylimidazolium bar (3)[b] | 0% | - |
| decabromoethyl-pillar[5]arene | | |
| + none[c] | 0% | - |
| + C₈ diazide bar (4)[c] | 0% | - |
| + C₁₀ diazide bar (5)[c] | 0% | - |

FIG. 7A

| Pseudo-rotaxane (macrocycle + bar) | % Depletion[a] | δ (ppm)[a] |
|---|---|---|
| α-cyclodextrin | | |
| + none | 0% | - |
| + C₅ diethylimidazolium bar (2) | 30% | +132 |
| + C₈ diethylimidazolium bar (3) | 0% | - |
| + C₁₀ diethylimidazolium bar (1) | 0% | - |
| β-cyclodextrin | | |
| + none | 0% | - |
| + C₅ diethylimidazolium bar (2) | 0% | - |
| + C₈ diethylimidazolium bar (3) | 0% | - |
| + C₁₀ diethylimidazolium bar (1) | 0% | - |
| γ-cyclodextrin | | |
| + none | 0% | - |
| + C₅ diethylimidazolium bar (2) | 43% | - |
| + C₈ diethylimidazolium bar (3) | 52% | +128 |
| + C₁₀ diethylimidazolium bar (1) | | +128 |

FIG. 7B

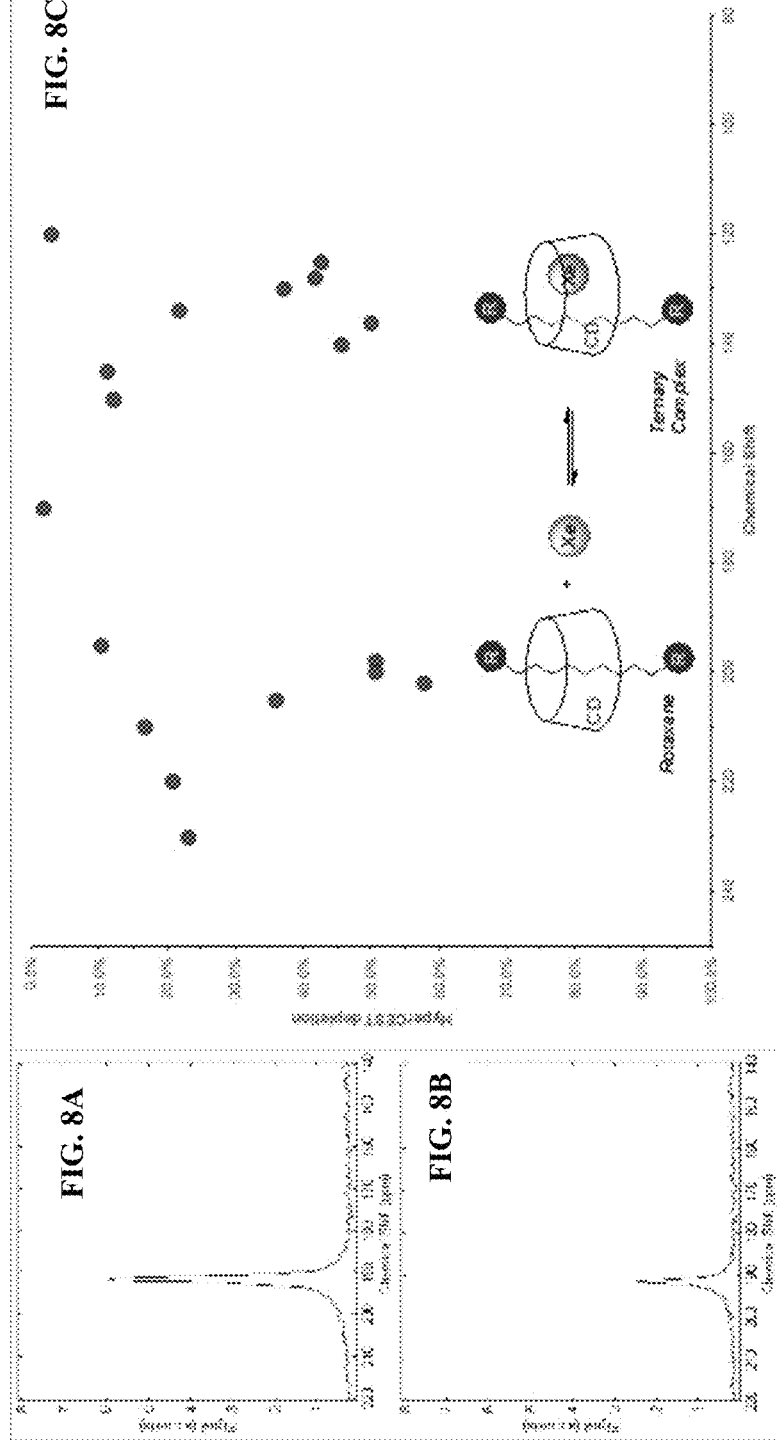

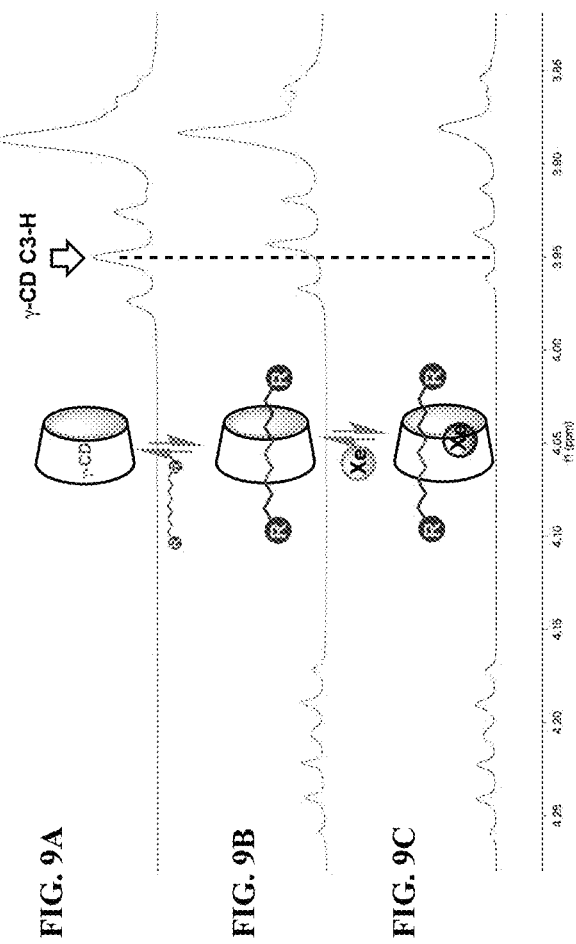

ROTAXANE-TYPE PROBE FOR MOLECULAR IMAGING

CROSS-REFERENCE TO RELATED APPLICATIONS

This application claims priority to and the benefit of U.S. provisional patent application Ser. No. 62/477,811, filed Mar. 28, 2017, which application is incorporated herein by reference in its entirety.

FIELD OF THE INVENTION

The invention relates to imaging probes and biosensors, and related processes. More specifically, the invention employs reversible encapsulation of the noble gas, xenon, in rotaxane and pseudo-rotaxane molecules for detection by hyperpolarized xenon-129 magnetic resonance imaging (HP Xe MII) and other molecular imaging technologies.

BACKGROUND OF THE INVENTION

Hyperpolarized (HP) xenon-129 based magnetic resonance imaging (MII) agents have the potential to become a molecular imaging modality with similar sensitivity to positron emission tomography (PET), but with theoretically better spatial resolution, no ionizing radiation and lower cost. HP gas MII takes advantage of the signal enhancement provided by the hyperpolarization of the noble gas, that is, aligning the spins of a majority of the nuclei with an external magnetic field to provide a signal enhancement up to 100,000 times greater than thermally polarized nuclei.[1] HP gas MM is an ideal modality for imaging of the lungs,[2] but because xenon is hydrophobic, it diffuses throughout the whole body following inhalation. Xenon deposits particularly well in lipid-rich tissues, so high-resolution, three-dimensional images can be obtained by detecting the HP Xe that is deposited in various fatty tissues, such as the brain.[3-5]

HP-Xe atoms cannot, by themselves, be tuned to target particular regions in the body, but targeted HP Xe biosensors that are capable of binding both biochemical receptors and xenon atoms in vivo have been postulated as a new molecular imaging platform. Numerous prototypes have been developed,[6-22] though targeted HP Xe biosensors have yet to be used for imaging in a living animal.

HP Xe MRI biosensors consist of two functional parts, a binding component and a detection component that are joined by a covalent tether (FIG. 1A). The binding component is an affinity tag or antibody that binds to a specific analyte or biochemical receptor, allowing for the detection and characterization of specific biochemical phenomena. The detection component for a HP Xe biosensor is usually a supramolecular cage-like structure that can encapsulate a xenon atom, such as cryptophane-A or cucurbit[6]uril (CB6) (FIG. 1B).

For in vivo HP-Xe biosensor imaging, a subject inhales the magnetically active HP Xe, and the imaging biosensor is administered via an injection (FIG. 2A). After dissolved Xe gas has circulated through the subject's body and the biosensor has attached to the desired molecular target, the Xe will be reversibly encapsulated by the xenon cage in a traditional host-guest interaction. If the reversible encapsulation is slow on the NMR time scale, it will produce a unique chemical signal in the $^{129}$Xe NMR spectrum that can be transformed into a three-dimensional image.

The Hyperpolarized Chemical Exchange Saturation Transfer (HyperCEST) pulse sequence is a scheme for amplifying HP Xe NMR signals by taking advantage of the continual diffusion of Xe atoms in and out of a Xe-encapsulating cage molecule. This phenomenon allows for the detection of picomolar concentrations of a HP-Xe biosensor.[23-26] Because the binding of the Xe is reversible, but slow on the NMR timescale, the $^{129}$Xe spectrum of a biosensor contains two peaks, one for unbound Xe and one for the xenon that is encapsulated by the biosensor. By irradiating the HP Xe atoms inside the supramolecular cage at their unique chemical shift offset frequencies, the Xe atoms inside the cage molecules become depolarized. When these depolarized Xe atoms exchange with the HP Xe atoms from the pool of dissolved Xe atoms, there is a reduction in signal from the pool of dissolved phase Xe atoms (FIG. 1C). The HyperCEST technique provides a $10^4$-$10^5$ signal enhancement. When combined with hyperpolarization of the nuclei, a theoretical signal enhancement of up to a billion times above thermally polarized nuclei can be achieved.[27]

We recently disclosed the first in vivo images of a HP Xe probe in a live animal using the non-targeted Xe cage, CB6 (FIG. 2A).[28] We successfully detected the presence of CB6 in the brain and the vasculature near the brain, liver, aorta, heart, kidneys, and following its renal clearance, in the bladder (FIG. 2B). This work demonstrates that xenon-imaging biosensors are detectible in vivo, a long-standing challenge in the advancement of this imaging technology.

Despite the seminal work of Pines and colleagues over two decades ago[29] and our recent demonstration of in vivo HyperCEST imaging, targeted HP Xe MM biosensors have yet to be used for in vivo imaging in a whole animal. The development of targeted probes has not been slowed by a lack of interest in the techniques or by barriers in Mill technology. The problem is more fundamental: conventional supramolecular hosts that encapsulate xenon are extremely difficult and cumbersome to synthesize and functionalize for effective delivery to various regions, tissues or specific subcellular targets, so sufficient quantities of biosensors for in vivo imaging are simply not available. For example, in one recent report, the Dmochowski group conjugated a cryptophane-A to folic acid to yield a potential biosensor for cancer and it took 20 non-linear steps to synthesize the final product (see, Khan, N., et al., *Bioconjugate Chem.*, 2015, 26 (1), 101-109). Therefore, there is a strong need for an HP Xe biosensor that can be synthesized in a simpler way and with higher yield.

SUMMARY OF THE INVENTION

In a first aspect, the invention relates to a supramolecular complex that can be used in molecular imaging applications as a biosensor, the complex comprising: (a) a macrocycle host having a hydrophobic cavity; and (b) an axle/bar comprising a molecular chain functionalized with an affinity tag for a target in a biological subject, where the axle is threaded through the macrocycle cavity. In a feature, the affinity tag is at or near at least one end (or, terminal), preferably both ends, of the axle. During use and inside a subject, the supramolecular complex is further joined by (c) a xenon molecule, which becomes housed in the macrocycle host's cavity. In one feature, the macrocycle host is water-soluble and has a cavity that is large enough to at least accommodate the xenon molecule and the axle molecule at the same time. In an embodiment, the cavity is larger than about 6.5 Å, preferably is about 8.0 Å, and more preferably is about 8.3 Å, in inner diameter. In one feature, the axle is a relatively straight chain, e.g., an alkyl chain. In various embodiments, the axle has at least six carbons, e.g., a hexane. In some embodiments, the axle has 8, 9, or 10 carbons in its backbone. In some embodiments, the axle contains one or two hydrophobic rings, e.g. a benzene or naphthalene unit. In another feature, the axle is capped at each of its two ends with an end group, preferably hydrophobic, such as an ethylimidazolium group or an anthracene group. The end group can include the affinity tag.

In one embodiment, the macrocycle employed in the biosensor of the invention is a cyclodextrin, and preferably, γ-cyclodextrin. The axle molecule may be: 1,1'-(octane-1, 8-diyl)bis(3-ethyl-1H-imidazol-3-ium) dibromide, 1,1'-(decane-1,8-diyl)bis(3-ethyl-1H-imidazol-3-ium) dibromide, 1,8-diazidooctane, or 1,8-diazidodecane. In an embodiment, the affinity tag is thioflavin T.

In a second aspect, the rotaxane-type supramolecular complex of the invention is similar as described in connection with the first aspect except that the affinity tag is conjugated or otherwise affixed to the macrocycle host instead of the axle.

In other aspects, the invention features methods of making the biosensor of the invention, and methods of using such biosensors, e.g, in clinical settings.

The foregoing and other objects, aspects, features, and advantages of the invention will become more apparent from the following description and from the claims.

BRIEF DESCRIPTION OF THE DRAWINGS

The patent or application file contains at least one drawing executed in color. Copies of this patent or patent application publication with color drawings will be provided by the Office upon request and payment of the necessary fee.

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 1A: Schematic of a targeted HP-Xe MRI biosensor. FIG. 1B: Example of a cryptophane biosensor that targets integrin.[17] FIG. 1C: HyperCEST scheme.

FIG. 3 shows examples of host molecules with structural features that were tested for capturing xenon.

FIGS. 7A and 7B show HyperCEST data for rotaxane-type biosensors: (FIG. 7A) cucurbiturils and pillararene-based; (FIG. 7B) cycodextrin-based. [Note: [a] Samples were dissolved in water (2 mL, 10 mM), and 1D $^{129}$Xe spectrum were initially recorded and then a series of HyperCEST spectra were sequentially recorded using a series of off resonance pulses varying by 5 ppm. [b] Performed in $H_2O$/DMSO. [c] Performed in $CHCl_3$.]

FIGS. 8A-8C show FID and HyperCEST depletion spectra of γ-cyclodextrin with the $C_{10}$ diethylimidazolium bar ($1 \subset$ γ-CD). Free Induction Decay (FID) spectra of 10 mM γ-cyclodextrin with a 10-carbon ethyl imidazole bar following off-resonance (FIG. 8A) (+255 ppm) and on-resonance (+128 ppm) HyperCEST pulses (FIG. 8B). HyperCEST depletion z-spectrum (FIG. 8C) of 10 mM γ-cyclodextrin with the $C_{10}$ diethylimidazolium bar ($1 \subset$ γ-CD). Each data point indicates the HyperCEST depletion when the molecule is irradiated with a HyperCEST pulse at a given chemical shift offset. A maximum HyperCEST depletion of 52% was observed.

FIGS. 9A-9C show $^1$H NMR evidence for the formation of the ternary complex in embodiments of the invention. FIG. 9A: $^1$H NMR spectrum of γ-cyclodextrin. FIG. 9B: $^1$H NMR spectrum after addition of 1 equivalent of $C_{10}$ diethylimidazolium bar. FIG. 9C: $^1$H NMR spectrum after addition of 1.5 atm xenon.

FIG. 11A shows one strategy according to an embodiment of the invention as to how to make a rotaxane; FIG. 11B shows an alternative strategy according to a second embodiment.

DETAILED DESCRIPTION OF THE INVENTION

Unless otherwise noted, technical terms are used according to conventional usage.

As used in the specification and claims, the singular form "a", "an", or "the" includes plural references unless the context clearly dictates otherwise. For example, the term "a cell" includes a plurality of cells including mixtures thereof.

As used herein, "about" means within plus or minus 10%. For example, "about 1" means "0.9 to 1.1", "about 2%" means "1.8% to 2.2%", "about 2% to 3%" means "1.8% to 3.3%", and "about 3% to about 4%" means "2.7% to 4.4%."

As used herein, the term "subject" refers to any animal (e.g., a mammal), including, but not limited to humans, non-human primates, rodents, canines, and the like, which is to be the recipient of a particular treatment. Typically, the terms "subject" and "patient" are used interchangeably herein in reference to a human subject.

According to principles of the present invention, a xenon-capturing scaffold or framework is conjugated to affinity tags to bind a wide variety of targets inside a subject, where such targets can be biological markers that indicate diseases or disease-prone conditions. The detection of such targets can then be used for diagnostic or monitoring purposes. Examples of such targets include various reporter gene expressions, cancer-associated receptors (HER2 for breast cancer diagnosis, for instance), pathogen, toxins, and so on. Preferred embodiments of affinity tags include detectable labels, e.g., fluorescent dyes or radioactive isotopes.

Figure 4A:
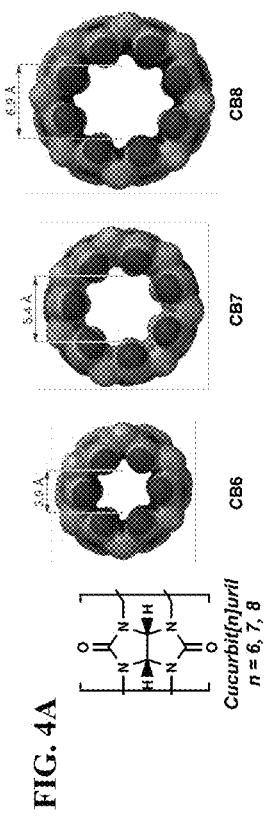
FIG. 4A: Electrostatic potential maps and chemical structures of cucurbiturils and cyclodextrins.

Referring to FIG. 3: until recently, the hollow, ball-shaped molecular cages known as cryptophanes appeared to be privileged structures in the field of HP-Xe imaging. Cryptophane-A contains a hydrophobic core with a volume of 95 Å$^3$,[10] and is capable of reversibly binding xenon with a $k_a$ of 3 kM$^{-1}$, with a residence time of 0.5-8 ms at room temperature[11]. Despite it's more tube-like structure, cucurbit[6]

uril (CB[6]) is also capable of binding xenon with a comparable affinity ($k_a$=200 M$^{-1}$),[12] but its larger derivatives, cucurbit[7]uril (CB[7]) and cucurbit[8]uril (CB[8]), do not show any affinity for xenon, as observed by $^{129}$Xe NMR (FIG. 4A). Additionally, α, β and γ-cyclodextrins (CD), which are truncated cone-shaped macrocycles composed of six, seven or eight D-glycopyranoside units, have hydrophobic cavities with minimum diameters of 5.3 Å, 6.5 Å and 8.3 Å, respectively (FIG. 4A). CDs are non-toxic and water-soluble. As it turned out, α, β and γ-CD either fail to bind xenon in aqueous media, or the reversible binding has too fast of an exchange rate to be detectable by $^{129}$Xe NMR at room temperature.[13b]

Figure 4B:
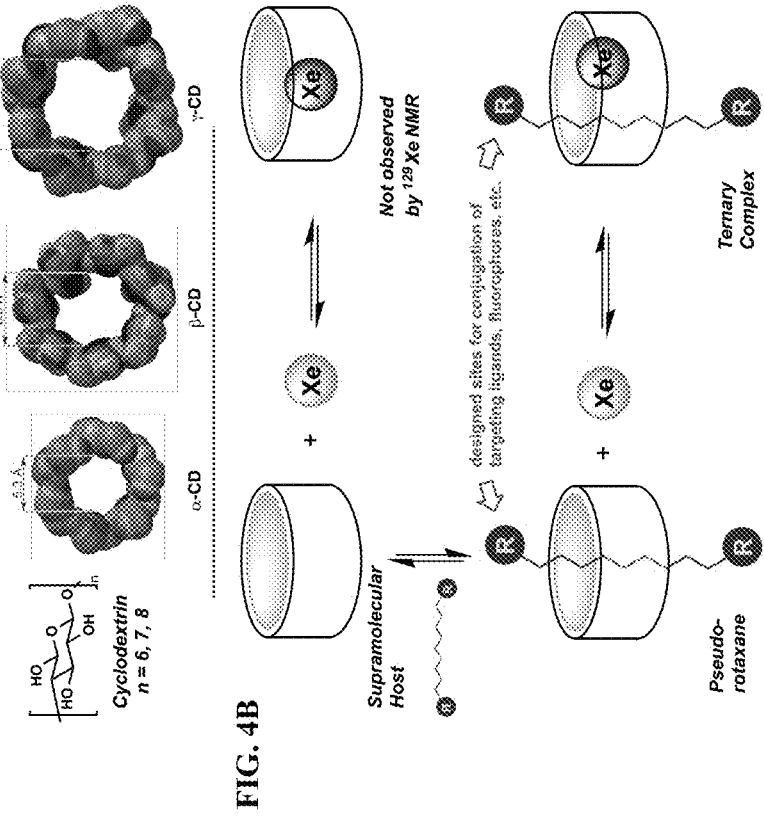
FIG. 4B: Binding of xenon via formation of a ternary complex, according to embodiments of the invention.

According to a principle of the present invention, macrocycles that are too large to bind xenon on their own, such as the cyclodextrins, could be threaded with an axle molecules, such as long alkyl chains, to create rotaxane-type, including proto-rotaxane and pseudo-rotaxane, complexes that are capable of forming a ternary complex with xenon (FIG. 4B). Rotaxanes are supramolecular species composed of a molecular axle that is threaded through a tube-shaped host, creating a non-covalently bound structure.[13c] In order to serve as a molecular probe, the inner diameter of the rotaxane's macrocycle must be large enough to fit both the molecular axle and a xenon atom in its hydrophobic core. However, a macrocycle that is too large would not be detectable using HyperCEST because the xenon would exchange in and out of the host at a rate that is too high to support HyperCEST detection. We designed three classes of pseudo-rotaxanes or rotaxanes to determine their potential as the imaging component of HP-Xe biosensors: CB-based pseudo-rotaxanes, pillararene-based pseudo-rotaxanes, and CD-based pseudo-rotaxanes.

The affinity tag can be conjugated or otherwise affixed to either part of the rotaxane-type supramolecular complex of the present invention, i.e., the macrocycle host or the axle molecule. However, according to an embodiment of the invention, the rotaxane-type biosensor of the invention is not synthesized by covalently tethering the affinity tag to the xenon host; rather, the affinity tag is conjugated to the axle bar, and the tethering of the affinity tag to the macrocycle is then accomplished via classic supramolecular chemistry relying primarily on hydrophobic interactions, which, coincidentally, are the same forces that are required for efficient xenon binding.

EXAMPLES

Example 1

Figures 5A, 5B:
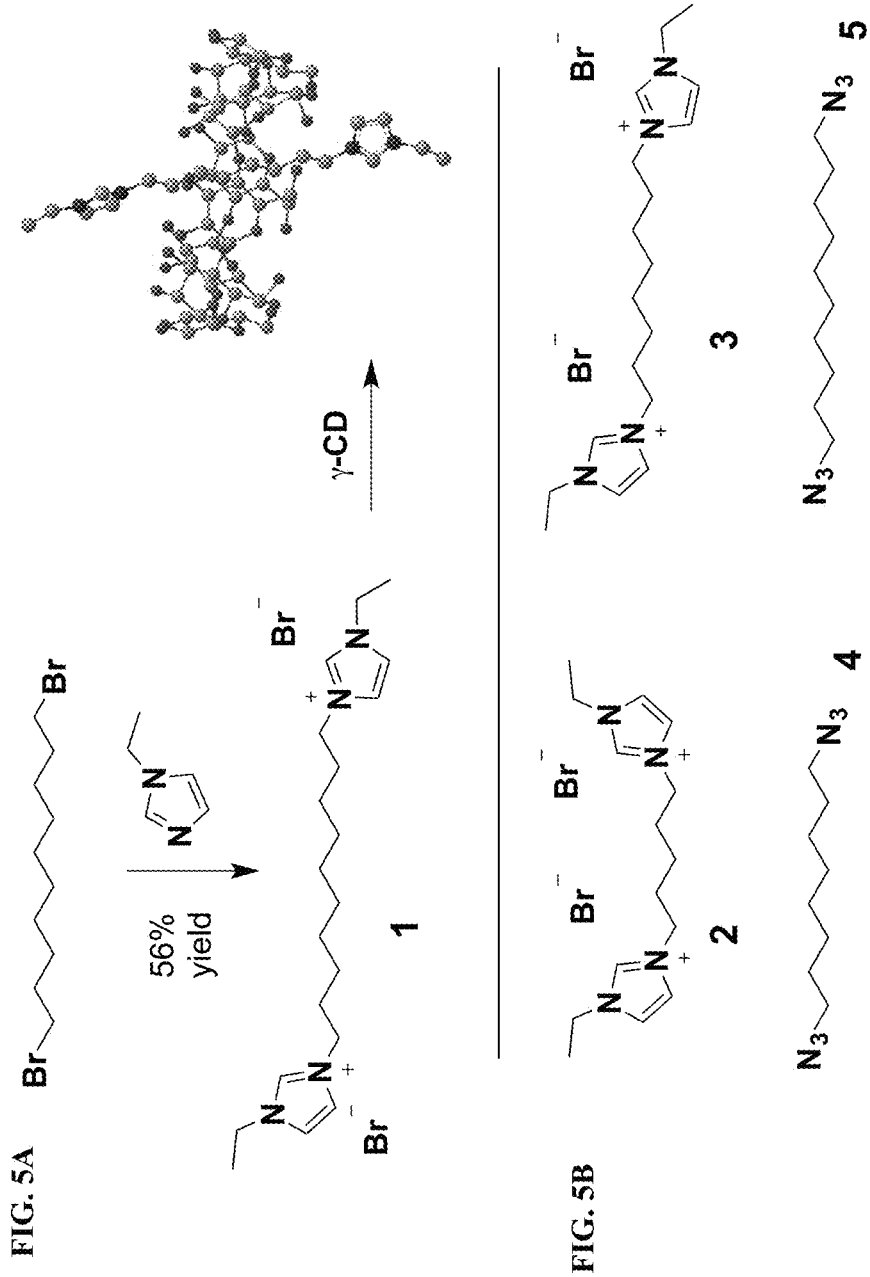
FIG. 5A: Synthesis of the $C_{10}$ dietylimidazolium bar (1) and its incorporation into γ-CD to form a pseudo-rotaxane, $1 \subset$ γ-CD.
FIG. 5B: Other bars tested in pseudo-rotaxanes: $C_5$ dietylimdazolium bar (2), $C_8$ dietylimdazolium bar (3), $C_8$ diazide bar (4) and $C_8$ diazide bar (5).

In the following exemplary embodiments, we found: the rotaxane-type biosensor can be readily synthesized and conjugatable; and the molecule is MR detectable by displaying a HyperCEST effect. Towards the first aspect, we found that pillararenes were relatively easy to synthesize and CB and CD macrocycles are both commercially available. Each of the host macrocycle molecules listed in FIG. 4A (CB6, CB7, CB8, α, β and γ-CD) was threaded with five, eight and ten-carbon molecular axles/threads that each contained a pair of terminal ethylimidazolium groups, which served to enhance the water solubility of the greasy alkanes and enabled facile detection by mass spectrometry (FIG. 5A). Furthermore, similar moieties with attached affinity tags can be created following the same or similar rationales by one of ordinary skills in the art. For example and referring to FIG. 5B, azide-containing threads were conjugated to affinity tags via Hugsien cyclo-addition and synthesized for the present invention (4 and 5). In all cases studied, the rapid formation of threaded complexes was observed by NMR, though most cases showed rapid host-guest exchange on the NMR time scale. Subsequent analysis by $^{129}$Xe NMR quickly identified the preferred scaffolds that combined the desired attributes of facile synthesis with MR detectability via HyperCEST.

Figure 6:
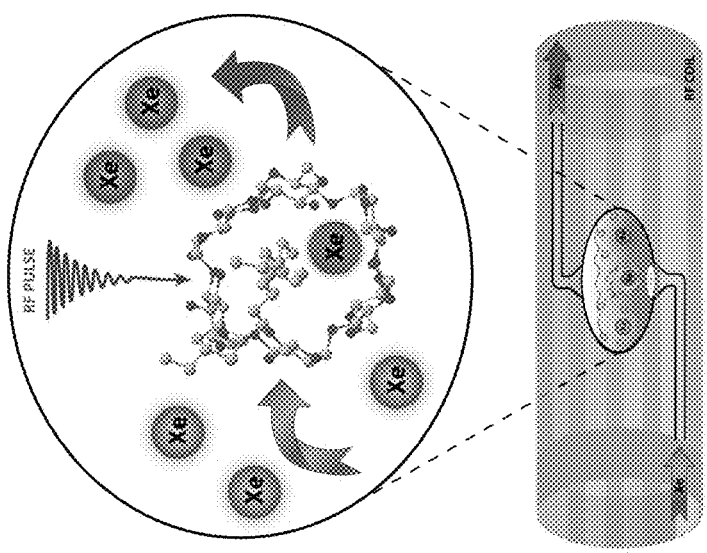
FIG. 6 schematically illustrates an experimental setup for testing the biosensor of the present invention.

For the HP-Xe studies, we used a custom-built fritted phantom inside of a custom dual tuned $^{1}$H/$^{129}$Xe radiofrequency (RF) coil to acquire all free induction decay (FID) spectra (FIG. 6). Rotaxane-type biosensor molecules, dissolved in water and/or DMSO, were placed inside the fritted phantom, and HP $^{129}$Xe was introduced below the fritted phantom that created microbubbles that rose vertically through the sample. A series of saturation pre-pulses at a variety of chemical shift offsets were loaded into the user interface software of the GE Achieva 3T MR scanner. Spectra with different saturation pre-pulses were acquired approximately every six seconds.

Referring specifically to the example shown in FIG. 6, 10 mM of γ-cyclodextrin with a $C_{10}$ diethylimidazolium bar (1 ⊂ γ-CD) dissolved in water was placed inside of a fritted phantom and placed inside an NMR RF coil. Hyperpolarized xenon was introduced into the phantom via a glass frit that produced microbubbles that dissolved in the solution. The HP-Xe atoms diffused in and out of the CD cage. An RF saturation pulse was applied at the Xe-CD chemical shift offset frequency depolarizing the $^{129}$Xe within the CD. The depolarized $^{129}$Xe diffused out of the CD and was replaced by an HP-Xe atom. This resulted in a reduction in the pool of HP Xe in solution thereby depleting the NMR signal, which indicates the presence of the probe molecule. The absence of an Xe imaging probe in the solution would result in no depletion of the dissolved phase Xe signal.

Referring now to results shown in FIG. 7, our initial studies commenced with the analysis of cucurbiturils. Irradiation at +128 ppm (relative to the peak corresponding to dissolved xenon) produced a 67% depletion with CB6, thus confirming that our experimental method was reliable. Various threaded complexes of CB6, CB7 and CB8 were then synthesized and subjected to the same HyperCEST protocol. However, none of the pseudo-rotaxanes could be detected by HyperCEST, indicating that there might not be sufficient space in the cavity of the some supramolecular complex (likely true for complexes like 1 ⊂ CB6) or that that xenon exchanges too rapidly in and out of the complex to be detected (possibly true for larger complexes like 1 ⊂ CB8).

Two different pillararene structures were also tested, but both suffered from poor water solubility. Consequently, organic co-solvents or non-ionic diazide bars (4 and 5) were employed. All pillararene-derived threaded complexes failed to produce a HyperCEST signal (FIG. 7A). This was surprising based on a recent report from the Cohen group.[34] We attempted to further these studies by applying HyperCEST saturation pulses and acquiring a HyperCEST depletion spectrum, but we were unable to observe a HyperCEST effect in pseudo-rotaxanes based on the pillararene macrocycle. We were neither able to detect the presence of a peak corresponding to a xenon-pillararene complex, nor a HyperCEST effect.

Figures 2A, 2B:
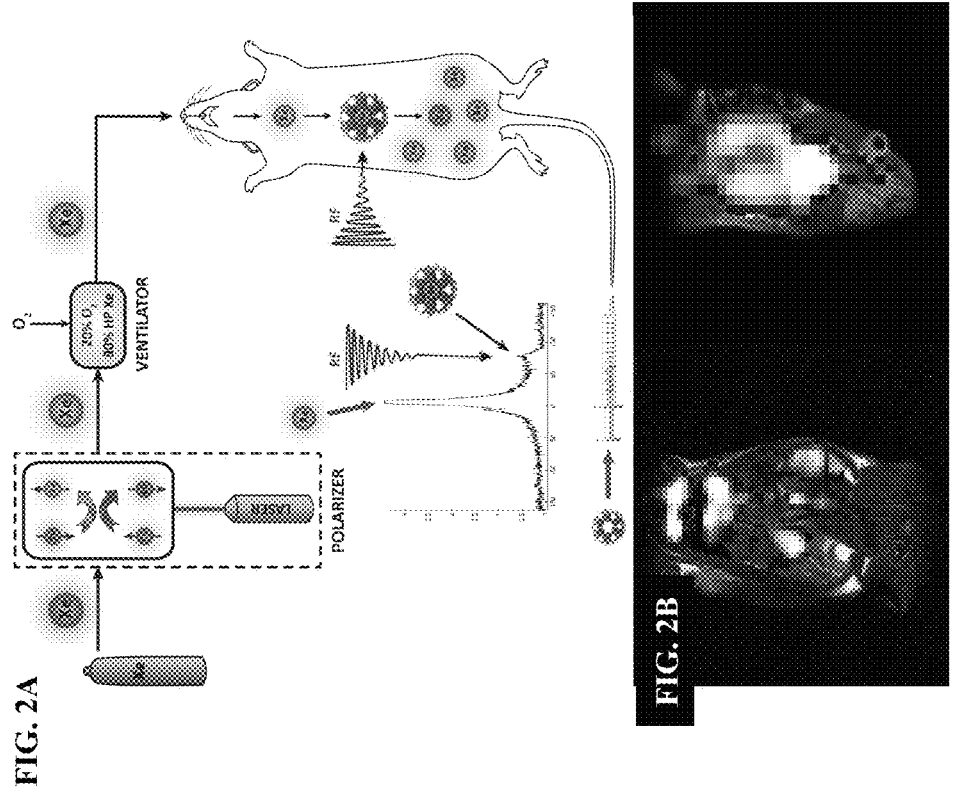
FIG. 2A: Scheme for in vivo imaging and HyperCEST saturation map of CB6 within the vasculature of a living rat.
FIG. 2B: CB6 was detected in the liver, kidneys, aorta, bladder (left) and brain (right) of the rat.[28]

However, according to the present invention, cyclodextrin-based pseudo-rotaxanes were found to reversibly encapsulate xenon and were detected by $^{129}$Xe magnetic resonance spectroscopy (FIG. 7B). A HyperCEST depletion of 30% for the pseudo-rotaxane formed by mixing α-cyclodextrin with the $C_5$ diethylimidazolium bar (2 ⊂ α-CD), 43% for γ-cyclodextrin pseudo-rotaxanes with the $C_8$ diethylimidazolium bar threaded through the cavity (3⊂γ-CD), and 52% for γ-cyclodextrin pseudo-rotaxanes with the $C_{10}$ diethylimidazolium bar threaded through its cavity (1⊂γ-CD). The maximum HyperCEST depletion for all three cyclodextrin-based rotaxanes occurred at approximately +128 ppm from the Xe gas phase signal. HyperCEST depletion spectra for 1⊂γ-CD are shown in FIG. 8. Importantly, the HyperCEST depletion for (1⊂γ-CD) was comparable to that of CB6, a xenon cage that we have recently shown to be amenable to in vivo HP Xe MRI (FIG. 2).

The data shown in FIGS. 7 and 8 were obtained using a Phillips Achieva 3T clinical whole-body MR scanner, which provides significant advantages over conventional NMR spectrometers, namely, the ability to perform whole-body imaging experiments. The use of a clinical scanner further supports eventual clinical translation of present embodiments in in vivo applications, which we recently demonstrated using a non-targeted $^{129}$Xe contrast agent.[14]

$^1$H NMR also confirms the formation of the ternary pseudo-rotaxane-xenon complex [(Xe•1)⊂γ-CD, FIG. 9]. Formation of the pseudo-rotaxane with γ-cyclodextrin and $C_{10}$ diethylimidazolium bar can be easily monitored by an upfield shift in the triplet corresponding to the proton attached to the C3 position in the cyclodextrin. This proton is positioned on the interior of the macrocycle, so it is shielded when the pseudo-rotaxane forms. Subsequent binding of xenon further shifts the C3-H peak upfield, indicating that the xenon also binds to the interior of the macrocyclic host.

Both isothermal caloriety (ITC) and NMR titration studies were performed to quantify the affinity of the molecular axles for their macrocyclic hosts. The association constant, $k_a$, for the most promising psuedo-rotaxane, 1⊂γ-CD, was determined by ITC to be $1.0 \times 10^4$ in pure water and $1.0 \times 10^2$ in fetal bovine serum. NMR titrations corroborated these data by measuring a $k_a$ of $8.8 \times 10^2$ M$^{-1}$ for the 1:1 host:guest complex of 1⊂γ-CD.[39] Despite this modest affinity, the formation of both the binary (1⊂γ-CD) and ternary [(Xe•1)⊂γ-CD] complexes is favorable and detectable by $^1$H and $^{129}$Xe NMR.[14]

Example 2

To demonstrate and test the utility of this new class of xenon-binding agents for the synthesis of targeted biosensors, we synthesized a potential molecular probe using thioflavin T (ThT) as part of the affinity tag. ThT is a fluorescent dye that has an affinity for binding to the β-amyloid plaques that have been implicated with the onset and progression of neurodegenerative diseases such as Alzheimer's disease (AD).[40] Using HP Xe biosensors such as this, the present invention provides clinical applications for studying the progression of AD and/or the efficacy of treatments for this and other diseases.

Figure 10B:
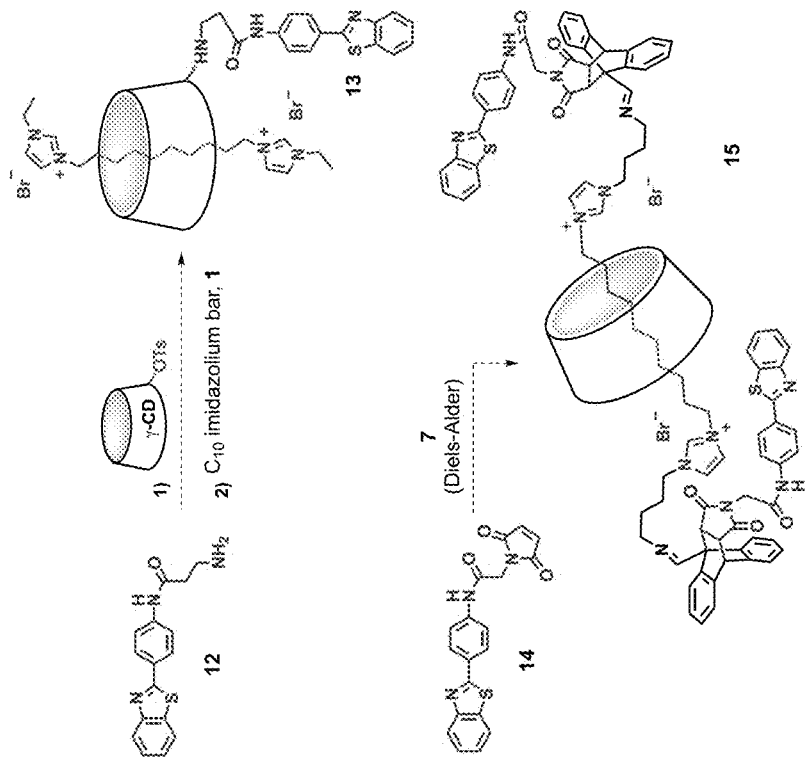
FIGS. 10A and 10B schematically illustrate facile synthesis of a biosensor embodiment according to the present invention, XCAL-1, in (FIG. 10A); and ways to synthesize additional embodiments conjugated with affinity tags in (FIG. 10B).
Figure 10A:
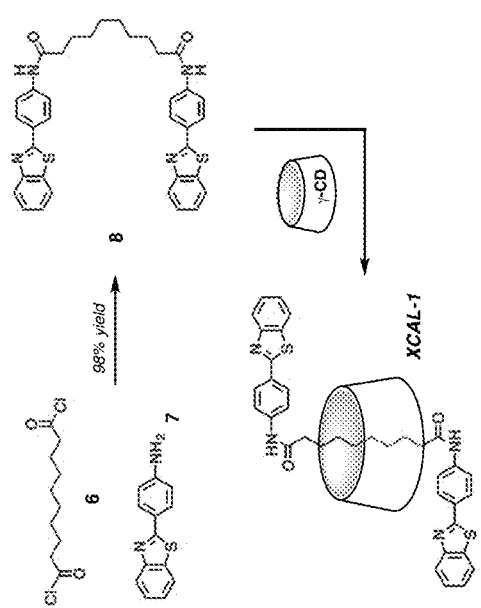

Referring now to FIG. 10A, the synthesis of this biosensor embodiment involves a simple acylation, followed by the formation of the pseudo-rotaxane. Both steps are nearly quantitative. As before, formation of the 1:1 complex was confirmed by $^1$H NMR studies, and the association constant for the pseudo-rotaxane was determined to be $2.0 \times 10^4$ M$^{-1}$. The reactions are simple and high-yielding, and can be scaled up for in vivo and ex vivo imaging studies and applications.

Referring now to FIG. 10B, in further embodiments, ThT continues to be used as the ligand in the affinity tag. Two alternative synthetic schemes were pursued. The first involves the conjugation of the ligand to the CD, where the second adds the ligand to the axle. We have synthesized mono-tosylated γ-CD by modifying the published procedure for β-CD (Byun, H.-S. et al., *Org. Synth.* 2000, 77, 225). This electrophile is reacted with a ThT-containing nucleophile such as 12 according to procedures that were developed for alkylating β-CD (Namazi, H. et al., *Polym. Int.* 2013, 63 (8), 1447-1455). Once this compound is synthesized, the $C_{10}$ imidazolium bar 1 can be used to synthesize a pseudo-rotaxane probe (13).

According to the second scheme, rotaxanes 8 and 15 were directly functionalized with the affinity tag/ligand using Diels-Alder reactions. The Diels-Alder reaction between anthracenes and maleimides has been categorized as a click reaction because it proceeds quickly and reliably (Gacal, B. et al., *Macromolecules* 2006, 39 (16), 5330-5336). As before, the formation of 13, 15 and derivatives thereof are assessed by $^1$H and $^{129}$Xe NMR experiments.

Example 3

In order to synthesize a more stable HP-Xe probe, rotaxanes are developed to contain large end groups on the alkyl chains that will prevent the dissociation of the macrocyclic hosts and their linear guests. Two strategies for synthesizing this kind of compound (FIG. 11) are employed.

We have found that the simple $S_N2$ displacement of alkyl bromides by imidazole nucleophiles in refluxing toluene is a reliable method for constructing the alkyl chains that form the threads/axles of rotaxane complexes. Consequently, a rotaxane was designed to contain anthracene stoppers/end groups that would prevent de-threading and imidazoles that would allow for facile construction of the thread. Klotz, E. J. F., et al., *J. Am. Chem. Soc.* 2006, 128 (48), 15374-15375. When the reaction shown in FIG. 11A was performed, the formation of complex 7 was observed as a precipitate, and its structure was confirmed by $^1$H NMR—supramolecular structure 7 appeared to be remarkably stable. Despite the potentially labile imine and N,N'-dialkyl imidazolium groups, no sign of decomposition was observed.

Figures 11A, 11B:
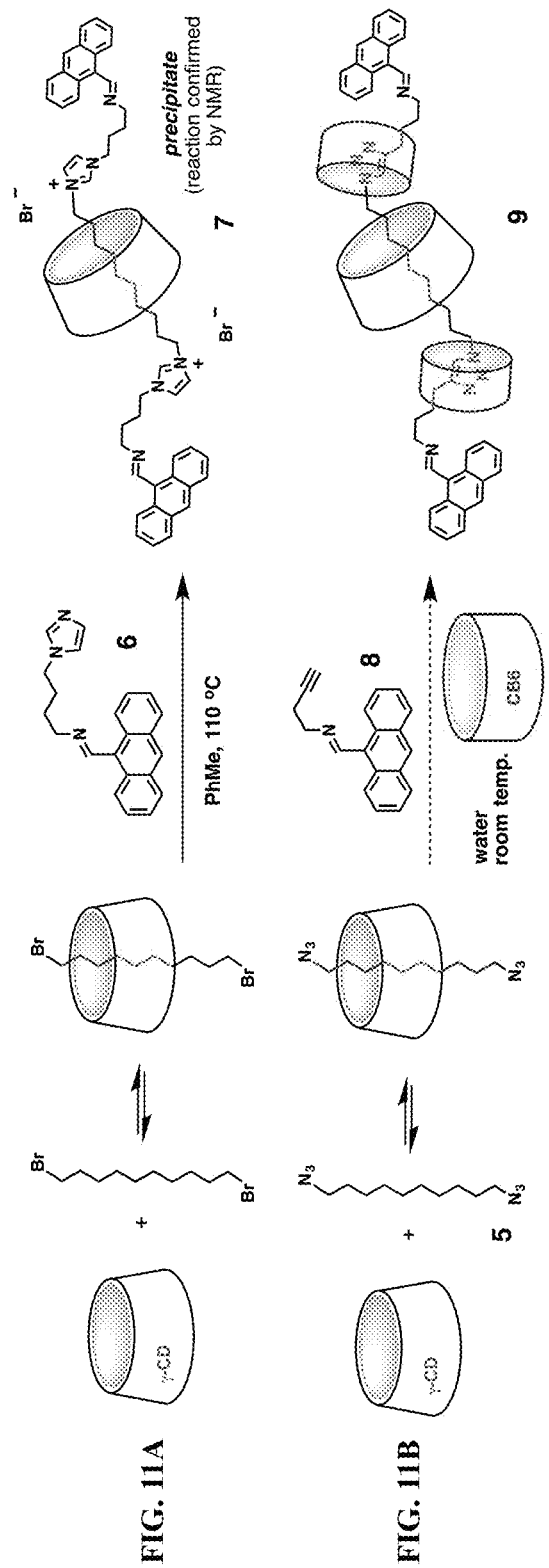
FIGS. 11A and 11B schematically illustrate the synthesis of second-generation rotaxane probes according to principles of the invention.

Referring now to FIG. 11B, a second rotaxane is synthesized using the CB6-catalyzed azide-alkyne cycloaddition. Hou, X., et al., *Chem. Soc. Rev.* 2016, 45, 3766-3780. The copper-free click reaction is the key step in a cooperative capture syntetic scheme that ensures that the central rotaxane ring, γ-CD, is threaded by the molecular axle prior to the end capping process.

Once the second-generation rotaxanes have been synthesized, their ability to bind xenon in solution is quantified by NMR titrations. Increasing amounts of xenon are condensed and added to degassed samples of the rotaxanes in J-Young tubes. Haouaj, El, M. et al., *J. Chem. Soc., Perkin Trans. 2* 2001, 804-807. As shown in FIG. 9, the binding of the xenon in the rotaxane's central cavity is indicated by a change in the chemical shift of the C3-H, and the movement of this peak as a function of xenon concentration is plotted to determine the $k_a$ and the stoichiometry of the xenon-rotaxane complex.

Example 4

After we have found the offset frequencies corresponding to the guest-host complexes shown in FIG. 7, we perform HyperCEST experiments over a range of temperatures. See Schröder, L. et al., *Phys. Rev. Lett.* 2008, 100 (25), 257603; Brotin, T. et al., *Eur. J. Org. Chem.* 2003, 2003 (6), 973-984. These experiments allow us to generate Arrhenius and Eyring plots for the xenon exchange processes, thus elucidating the terms $E_a$, $\Delta H^{\ddagger}$, $\Delta S^{\ddagger}$, and $\Delta G^{\ddagger}$ for each xenon-host interaction. These experiments are performed in water, plasma and whole blood to provide a framework for further in vivo studies.

Furthermore, x-ray quality crystals of the rotaxanes and pseudo-rotaxanes that provide HyperCEST spectra are grown both in the presence and absence of xenon, and are sent to crystallography laboratories for analysis. See Taratula, O. et al., *Nat Commun* 2010, 1, 148. These crystal structures are then used to calculate the volume of the hosts' xenon-binding hydrophobic cavities, and the size of their apertures using software such as Swiss PDB Viewer. Alternatively, DFT calculations are performed using commercial software packages (e.g. Spartan™) to predict the structures of the pseudo-rotaxane and rotaxane complexes and their ternary complexes with xenon. The diameters of the apertures that allow for xenon ingress and egress from the rotaxane hosts as well as the volumes of the hydrophobic cavities within the rotaxanes are compared to comparable data based on crystal structures of CB6 and cryptophane-A to correlate the host structure with HyperCEST kinetic and thermodynamic data. These experiments give a better understanding of the dynamic host-guest interaction that allows for HyperCEST imaging.

Technical Details

Nuclear Magnetic Resonance (NMR) HyperCEST Detection. Natural abundant $^{129}$Xe gas was polarized to 26-30% using a Xemed polarizer (Xemed, Durham, N.H., USA). 1.0 mL of sample was drawn into the glass frit cell using a syringe. The cell was then inserted into a custom RF coil tuned to the Larmor frequency of $^{129}$Xe (35.33 MHz) at 3T, where HP $^{129}$Xe gas was introduced to the vessel from the Tedlar bag in the pressure chamber which was pressurized at 35 kPa above atmosphere. The solution was mixed with HP $^{129}$Xe gas as it passed through the fine fitted disc and produced several microbubbles, which continuously dissolved into solution and exited the vessel through the outflow tube. The concentration of $^{129}$Xe at any point during the experiment was between 1-10 mM. A Philips Achieva 3T clinical scanner was used to collect all NMR spectra. The RF pulse length was determined with the use of the Ref $B_1$, a parameter of Philips MR scanners. The pulse length and flip angle were used to calculate the amplitude of the RF pulse and field strength. In this study, the B1 field strength was determined by the scanner to be 15.9 µT. In the acquisition of NMR spectra, a pulsed saturation pre-pulse train consisting of 96-20 ms 3-lobe sinc pulses with 0 ms pulse intervals was applied at various chemical shift offsets. Free induction decay (FID) spectra were acquired at various chemical shift frequency offsets, approximately 5 ppm apart. Each FID spectra was acquired approximately 6 seconds apart. Off-resonance FID spectra were obtained quarterly in this series and acquired with a saturation pre-pulse at +271 ppm off resonance from the gas phase peak. A HyperCEST depletion spectrum was collected for each sample (See Supplemental Information) by measuring HyperCEST depletion at various frequency offsets from the Xe gas phase peak. A minimum of three spectra were obtained at each of the various chemical shifts and a plot of the mean signal depletion as a function of the frequency of the chemical shift offset (z-spectrum) was produced. The mean signal-to-noise ratio (SNR) obtained from all control spectra for individual samples were used in the measurement of signal depletion. The SNR for each spectrum was calculated using MATLAB (MathWorks, Natick, Mass., USA). To measure signal depletion, the mean HyperCEST saturation spectrum SNR was subtracted from the mean control spectrum SNR. This difference was then divided by the mean control spectrum SNR to produce the signal depletion by the HyperCEST effect.

REFERENCES (1) Happer, W. *Rev. Mod. Phys.* 1972, 44, 169.

(2) Albert, M. S.; Cates, G. D.; Driehuys, B.; Happer, W.; Saam, B.; Springer, C. S.; Wishnia, A. *Nature*. 1994, 370, 199.

(3) Rao, M.; Ste art, N. J.; Norquay, G.; Griffiths, P. D.; Wild, J. M. *Magn. Reson. Med.* 2016, 75, 2227.

(4) Mazzanti, M. L.; Walvick, R P.; Zhou, X.; Sun, Y.; Shah, N.; Mansour, J.; Gereige, J.; Albert, M. S. *PLoS One* 2011, 6, e21607.

(5) Hane, F. T.; Imai, H.; Kimura, A.; Fuji ara, H.; Rao, M.; Wild, J. M.; Albert, M. S. In *Hyperpolarized and Inert Gas MRI: Theory and Applications in Research and Medicine*; Academic Press, 2016.

(6) (a) Pines, A.; Wemmer, D.; Spence, M.; Rubin, S. M. Functionalized active-nucleus complex sensor. US 20040062715A1, 2004; (b) Spence, M.; Rubin, S.; Dimitrov, I.; Ruiz, E.; Wemmer, D.; Pines, A.; Yao, S.; Tian, F.; Schultz, P. *Proc. Natl. Acad. Sci.* 2001, 98, 10654.

(7) Wang, Y.; 5, I. J. *Acc. Chem. Res.* 2016, 49, 2179.

(8) (a) Schröder, L. In *Hyperpolarized and inert gas MRI: From technology to application in research and medicine*; Albert, M. S., Hane, F. T., Eds.; Academic Press, 2016; (b) Schröder, L. *Phys Med* 2013, 29, 3.

(9) Schröder, L.; Lo ery, T.; Hilty, C.; Wemmer, D.; Pines, A. *Science* 2006, 314, 446.

(10) Fogarty, H. a.; Berthault, P.; Brotin, T.; Huber, G.; Desvaux, H.; Dutasta, J. P. *J. Am. Chem. Soc.* 2007, 129, 10332.

(11) Bartik, K.; Luhmer, M.; Dutasta, J. P.; Collet, A.; Reisse, J. *J. Am. Chem. Soc.* 1998, 120, 784.

(12) El Haouaj, M.; Luhmer, M.; Ko, Y. H.; Kim, K.; Bartik, K. *J. Chem. Soc. Perkin Trans.* 2 2001, 2, 804.

(13) (a) Sharma, Neha; B., Ashish, *Drug Delivery* 2016, 23, 729; (b) Herbstein, F. H. *Crystalline Molecular Complexes and Compounds: Structures and Principles*; Oxford Scholarship, 2005; (c) Klotz, E. J. F.; Claridge, T. D. W.; Anderson, H. L. *J. Am. Chem. Soc.* 2006, 128, 15374.

(14) Unpublished data. Hane, F. T.; Li, T.; Smylie, P.; Pellizzari, R. M.; Plata, J. A.; DeBoef, B.; Albert, M. S., submitted September 2016.

(15) Chaffee, K. E.; Fogarty, H. a.; Brotin, T.; Goodson, B. M.; Dutasta, J.-P. P. *J. Phys. Chem. A* 2009, 113, 13675.

(16) Stevens, T.; Palaniappan, K.; Ramirez, M.; Francis, M.; Wemmer, D.; Pines, A. *Magn. Reson. Med.* 2013, 69, 1245.

(17) Mynar, J. L.; Lo ery, T. J.; Wemmer, D. E.; Pines, A.; Frechet, J. M. J. *J. Am. Chem. Soc.* 2006, 128, 6334.

(18) Bai, Y.; Hill, P. A.; Dmocho ski, I. *J. Anal. Chem.* 2012, 84, 9935.

(19) Wang, Y.; Dmocho ski, I. *Chem. Commun.* 2015, 51, 8982.

(20) Schnurr, M.; Sloniec-Myszk, J.; Döpfert, J.; Schröder, L.; Hennig, A. *Angew. Chem. Int. Ed. Engl.* 2015, 54, 13444.

(21) Hane, F.; Smylie, P.; Li, T.; Ruberto, J.; Do hos, K.; Ball, I.; Tomanek, B.; DeBoef, B.; Albert, M. *Contrast Media Mol. Imaging* 2016, 11, 285.

(22) Aime, S.; Delli Castelli, D.; Terreno, E.; Transfer, S.; Using, A. *Angew. Chemie-Int. Ed.* 2005, 44, 5513.

(23) Stevens, T. K.; Ramirez, R. M.; Pines, A. *J. Am. Chem. Soc.* 2013, 135, 9576.

(24) Shapiro, M. G.; Ramirez, R. M.; Sperling, L. J.; Sun, G.; Sun, J.; Pines, A.; Schaffer, D. V; Bajaj, V. S. *Nat. Chem.* 2014, 6, 629.

(25) Bai, Y.; Wang, Y.; Goulian, M.; Driks, A.; Dmochoski, I. J. *Chem. Sci.* 2014, 5, 3197.

(26) Wang, Y.; Roose, B. W.; Philbin, J. P.; Doman, J. L.; Dmocho ski, I. J. *Angew. Chemie* 2015, 55, 1733.

(27) Riggle, B. A.; Wang, Y.; Dmocho ski, I. J. *J. Am. Chem. Soc.* 2015, 137, 5542.

(28) Se ard, G. K.; Bai, Y.; Khan, N. S.; Dmocho ski, I. *J. Chem. Sci.* 2011, 2, 1103.

(29) Rose, H. M.; Witte, C.; Rossella, F.; Klippel, S.; Freund, C.; Schröder, L. *Proc. Natl. Acad. Sci.* 2014, 111, 11697.

(30) Kotera, N.; Tassali, N.; Léonce, E.; Boutin, C.; Berthault, P.; Brotin, T.; Dutasta, J. P.; Delacour, L.; Traoré, T.; Buisson, D. A.; Taran, F.; Coudert, S.; Rousseau, B. *Angew. Chemie Int. Ed.* 2012, 51, 4100.

(31) Tassali, N.; Kotera, N.; Boulard, Y.; Rousseau, B.; Dubost, E.; Brotin, T.; Dutasta, J.; Berthault, P. *Anal. Chem.* 2014, 86, 1783.

(32) Do hos, K. M.; Fox, M. S.; Ball, I. K.; Li, T.; Gajaada, G.; Wentzell, J.; DeBoef, B.; Albert, M. S. In *International Society for Magnetic Resonance in Medicine Annual Meeting*; 2014; p 3537.

(33) Khan, N. S.; Riggle, B. A.; Se ard, G. K.; Bai, Y.; Dmocha ski, I. J. *Bioconjug. Chem.* 2015, 26, 101.

(34) Adiri, T.; Marciano, D.; Cohen, Y. *Chem. Commun.* 2013, 49, 7082.

(35) Schnurr, M.; Sydo , K.; Rose, H. M.; Dathe, M.; Schröder, L. *Adv. Healthc. Mater.* 2015, 4, 40.

(36) Klippel, S.; Döpfert, J.; Jayapaul, J.; Kunth, M.; Rossella, F.; Schnurr, M.; Witte, C.; Freund, C.; Schröder, L. *Angew. Chemie Int. Ed.* 2014, 53, 493.

(37) Kunth, M.; Witte, C.; Hennig, A.; Schröder, L. *Chem. Sci.* 2015, 6, 6069.

(38) Kunth, M.; Witte, C.; Schröder, L. *NMR Biomed.* 2015, 28, 601.

(39) Tablet, C.; Matei, I.; Hillebrand, M. In *Stoichiometry and Research-The Importance of Quantity in Biomedicine*; InTech, 2012; pp 47-76.

(40) Khurana, R.; Coleman, C.; Ionescu-Zanetti, C.; Carter, S. A.; Krishna, V.; Grover, R. K.; Roy, R.; Singh, S. *J. Struct. Biol.* 2005, 151, 229.

While the present invention has been particularly shown and described with reference to the structure and methods disclosed herein and as illustrated in the drawings, it is not confined to the details set forth and this invention is intended to cover any modifications and changes as may come within the scope and spirit of the following claims. All publications and patent literature described herein are incorporated by reference in entirety to the extent permitted by applicable laws and regulations.

What is claimed is:

1. A supramolecular complex useful as a biosensor, comprising:
   (a) a macrocycle host defining a hydrophobic cavity;
   (b) an axle comprising a molecular chain functionalized with an affinity tag for a target inside a biological subject, wherein the affinity tag is at one or both ends of the molecular chain, and wherein the axle is threaded through the macrocycle cavity; and
   (c) a xenon atom, wherein the cavity of the macrocycle host is large enough to accommodate and reversibly encapsulate both a cross section of the axle and the xenon atom at the same time.

2. The supramolecular complex of claim 1, wherein the macrocycle host is water-soluble.

3. The supramolecular complex of claim 1, wherein the xenon atom is dissolved in a solution.

4. The supramolecular complex of claim 1, wherein the macrocycle host defines a cavity that is larger than about 6.5 Å in inner diameter.

5. The supramolecular complex of claim 1, wherein the macrocycle host is a cyclodextrin.

6. The supramolecular complex of claim 5, wherein the macrocycle host is a γ-cyclodextrin.

7. The supramolecular complex of claim 1, wherein the axle comprises an alkyl chain.

8. The supramolecular complex of claim 7, wherein the axle has at least five carbons in its backbone.

9. The supramolecular complex of claim 1, wherein the axle is capped with a hydrophobic end group at each of its two ends, at least one of the end groups being or comprising the affinity tag.

10. The supramolecular complex of claim 1, wherein the affinity tag comprises a ligand selected for its affinity for a biological target inside a subject.

11. The supramolecular complex of claim 1, wherein the affinity tag comprises a detectable label.

12. The supramolecular complex of claim 11, wherein the affinity tag comprises a fluorophore.

13. The supramolecular complex of claim 1, wherein the affinity tag comprises thioflavin T.

14. The supramolecular complex of claim 1, detectable by xenon-based magnetic resonance imaging or spectroscopy.

15. A biosensor comprising:
   (a) a cyclodextrin molecule defining a cavity;
   (b) an alkyl chain molecule functionalized with an affinity tag at one or each of its two ends, wherein the affinity tag has an affinity for a target inside a biological subject, and wherein the alkyl chain molecule is threaded through the cavity in the cyclodextrin; and
   (c) a xenon atom in the cavity of the cyclodextrin.

16. The biosensor of claim 15, wherein the affinity tag comprises a detectable label.

17. The biosensor of claim 15, wherein the affinity tag is part of an end group that also serves as a stopper to prevent de-threading.

18. The biosensor of claim 17, wherein the end group is hydrophobic.

19. The biosensor of claim 17, wherein the end group comprises an ethylimidazolium group or an anthracene group.

20. The biosensor of claim 15, wherein the xenon atom is xenon-129.

* * * * *